(12) United States Patent
Berg-Schultz et al.

(10) Patent No.: US 6,184,419 B1
(45) Date of Patent: Feb. 6, 2001

(54) α, β-UNSATURATED KETONES

(75) Inventors: Katja Berg-Schultz, Kaiseraugst; Jerzy A. Bajgrowiecz, Zürich, both of (CH)

(73) Assignee: Givaudan Roure (International) SA, Geneva (CH)

( * ) Notice: Under 35 U.S.C. 154(b), the term of this patent shall be extended for 0 days.

(21) Appl. No.: 09/568,257

(22) Filed: May 10, 2000

(30) Foreign Application Priority Data

May 27, 1999 (EP) .................................................. 99810461

(51) Int. Cl.$^7$ ............................ C07C 49/105; A61K 7/46
(52) U.S. Cl. ........................ 568/374; 568/375; 568/376; 568/377; 568/379; 512/8; 512/18; 512/22
(58) Field of Search ..................................... 568/375, 376, 568/377, 379, 374; 512/8, 18, 22

(56) References Cited

U.S. PATENT DOCUMENTS

| | | | |
|---|---|---|---|
| 4,615,830 | * 10/1986 | Sprecker et al. ...................... | 568/376 |
| 5,039,659 | * 8/1991 | Narula et ............................. | 568/377 |
| 5,118,865 | * 6/1992 | Chapuis et al. ....................... | 568/376 |
| 5,248,831 | * 9/1993 | Hopp et al. ........................... | 568/376 |

OTHER PUBLICATIONS

Marshall, J. A.., et al., *J. Org. Chem.*, vol. 30(8):2748–54 (1965).*
Stork, G., et al., *J. Amer. Chem. Soc.*, vol. 85(1):207–22 (1963).*
Cormier, R. A.., et al., *J. Amer. Chem. Soc.*, vol. 95(15):4873–84 (1973).*
Mukaiyama, T., et al., *J. Amer. Chem. Soc.*, vol. 96(23): 7503–9 (1974).*
Masso, T., et al., *Perfumer & Flavorist*, vol. 15:39–43 (1990).*
Morris, A. F. et al., *Perfumer & Flavorist*, vol. 16(4): 33–35 (1991).*

* cited by examiner

*Primary Examiner*—Alan Siegel
(74) *Attorney, Agent, or Firm*—Mark E. Waddell; Stephen M. Haracz; Bryan Cave LLP

(57) ABSTRACT

The present invention relates to new α,β-unsaturated ketones of formula I. The new compounds exhibit an intense, very long lasting green galbanum-type odor with fruity undertones. Compositions containing these novel compounds are also provided.

10 Claims, No Drawings

α, β-UNSATURATED KETONES

FIELD OF THE INVENTION

The present invention relates to new α,β-unsaturated ketones exhibiting a green-galbanum, fresh (metallic, undecatriene type) and fruity-pineapple and/or fruity-cassis odor, and to the use of these new compounds as fragrance materials in different compositions.

BACKGROUND OF THE INVENTION

Inexpensive floral fruity and green fragrances with intense pineapple and galbanum undertones are highly desirable in the art of perfumery. However, many of the natural and commercially available compounds, e.g. galbanum oil, are expensive and show a lack of stability. Moderately weak galbanum type compounds became available in the mid seventies including allyl amyl glycolate (International Flavor and Fragrance Inc.) and CYCLOGALBANATE® (Dragocco S.A.). Another member of this family, the allyl cyclopentyl glycolate is described in Sprecker, U.S. Pat. No. 4,735,932. However, glycolates are generally not stable in alkali, acid or oxidizing media.

1-(5,5-dimethyl-1-cyclohexen-1-yl)-4-penten-1-one is described by Morris, A. F.; Näf, F; Snowdon, R. L. in Perfumer & Flavorist 1991(16), 33 as an important compound for the perfumery. This compound possesses a powerful metallic odor reminiscent of galbanum with pineapple and hyacinth character that adds fresh, green, floral and fruity aspects to perfumes and perfumed products.

SUMMARY OF THE INVENTION

The present invention provides new compounds which have an intense and long lasting green galbanum type of odor accompanied by various fruity, mainly pineapple undertones.

One embodiment of the invention is a compound of formula I

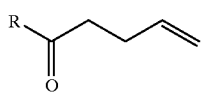

(I)

wherein R is a residue A

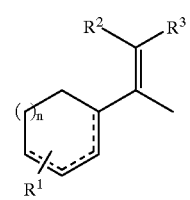

(A)

or a residue B

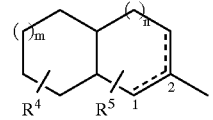

(B)

and $R^1$, $R^2$, $R^3$, $R^4$ and $R^5$ are independently hydrogen, methyl or ethyl, and $R^1$, $R^4$ and $R^5$ are at any position of the ring structure, n and m are independently 0, 1, 2 or 3 and the dotted lines in formula A, if desired, stand for a double bond and the dotted lines in formula B stand, for a double bond either in position 1 or 2. These examples have an intense, very long lasting green-galbanum type of odor with fruity undertones. These characteristics make the new compounds well suited for difficult functional perfumery applications, as well as for imparting unique green galbanum and fruity notes to fine perfumery products.

The above formulas include all different possible stereo- and double-bond isomers.

or residue B

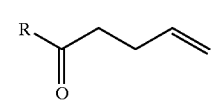

(B)

and $R^1$, $R^2$, $R^3$, $R^4$, and $R^5$ are independently hydrogen, methyl or ethyl, and further wherein $R^1$, $R^4$ and $R^5$ are located at any position of the ring structure, n and m are independently 0, 1, 2, or 3 and the dotted lines represent in formula A an optional double bond and in formula B a double bond either in position 1 or 2.

DETAILED DESCRIPTION OF THE INVENTION

It has surprisingly been found that compounds of Formula I

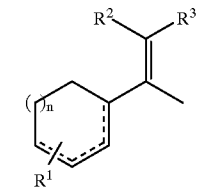

(I)

wherein R is a residue A

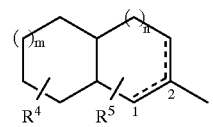

(A)

New compounds of formula Ia are preferred:

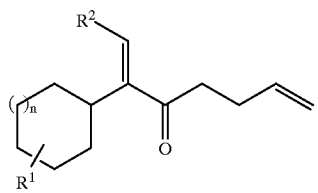

(Ia)

wherein $R^1$ and $R^2$ are independently hydrogen or methyl and n stands for 0 or 1.

Further preferred compounds are:

2-cyclohexylhepta-1,6-dien-3-one;

(E)-and (Z)-3-cyclohexylocta-2,7-dien-4-one;

2-cyclopentylhepta-1,6-dien-3-one;

1-(3,4,4a,5,6,7,8,8a-octahydronaphth-2-yl)pent-4-en-1-one; and 1-(1,4,4a,5,6,7,8,8a-octahydronaphth-2-yl)pent-4-en-1-one.

In addition to the above excellent qualities, it has been found that the compounds of the invention show outstanding diffusion and/or high substantivity, the latter meaning persistence of odor. The high diffusion and substantivity is well perceived on fabrics washed with a detergent or treated with a softener containing one or more of the new α,β-unsaturated ketones. The typical fresh green odor is already perceived very strongly on the wet fabric and later also on the dry material.

Due to the excellent odor and application qualities, the new compounds are excellent fragrances for use in any field of fine and functionary perfumery, such as perfumes, household products, laundry products, body care products, and cosmetics.

The new α,β-unsaturated ketones of formula I, wherein R is a residue of formula A, may be prepared according to procedures known in the art as shown in Scheme 1.

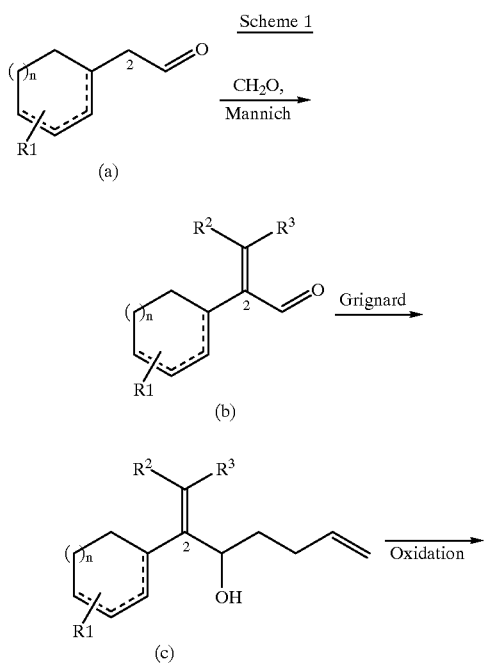

The starting materials of formula (a) in Scheme 1 may be prepared by oxidation of the corresponding alcohols. By methylenation with formaldehyde (Mannich reaction), aldehydes of formula (b) wherein $R^2$ and $R^3$ are hydrogen are obtained.

The α,β-unsaturated aldehydes corresponding to compounds of Formula I wherein R is a residue of formula A and $R^2$ and/or $R^3$ are not hydrogen may be prepared, for example, via cross-aldol condensation using Mukaiyama conditions followed by dehydration (T. Mukaiyama, K. Banno, K. Narasaka: J. Amer. Chem. Soc. 1974 (96), 7503).

Alternatively, the Grignard reaction may be carried out using appropriately substituted nitrites. This "one pot reaction" gives good yields of α,β-unsaturated ketones. 2-substituted-3-trimethylsilyloxypropionitriles are especially well suited for this transformation. The latter can be prepared, for example, from the respective cyclic ketones and ethyl cyanoacetate (according to J. A. Marshall, R. D. Carroll: J. Org. Chem. 1965 (30), 2748) followed by protection of the hydroxy-group with trimethylchlorosilane.

Another possible preparation of the α,β-unsaturated ketones of Formula I in which R is a residue A proceeds via Claisen transposition of the corresponding vinyl ether (See. e.g., T. Masso, A. Portella, E. Rus: Perfumer & Flavorist 1990 (15), 39) starting with the suitably substituted 3-butene-2-ones (prepared, e.g., according to R. A. Cormier, W. L. Schreiber, W. C. Agosta: J. Amer. Chem. Soc. 1973 (95), 4873).

The new α,β-unsaturated ketones of Formula I wherein R is a residue of formula B can be prepared from the corresponding bicyclic ketones according to the process illustrated in Scheme 2.

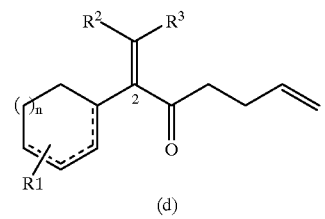

(d)

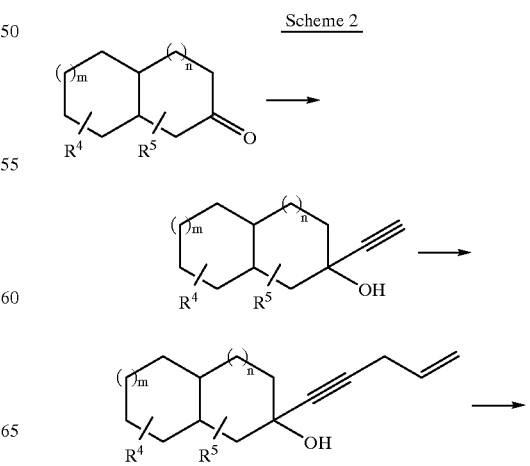

-continued

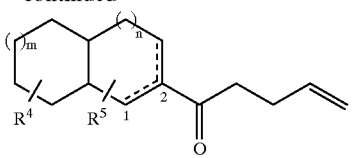

The starting ketones are either commercially available, or can be synthesized by Robinson annullation from the corresponding ketones with substituted or unsubstituted methyl vinyl ketones, followed by selective hydrogenation with Pd/C (see e.g., G. Stork, A. Brizzolara, H. Landesman, J. Szmuskovicz, R. Terrell: J. Amer. Chem. Soc 1963 (85), 207).

The α,β-unsaturated ketones wherein R is a residue of formula B, are generally obtained as mixtures of cis-/trans-isomers. The double bond is either in position 1 or 2. The odors of the different isomers are all of the same "green" type, however the GC thresholds may vary within broad ranges. A preferred compound is cis-1-(1,4,4a,5,6,7,8,8a-octahydronaphth-2-yl)pent-4-ene-1-one (n=m=1, and $R^4=R^5=H$), wherein the most powerful isomer has a GC-threshold of only 10 pg/l.

The new odorants may be combined with numerous odorant ingredients of natural and/or synthetic origin. The range of the natural odorants includes, in addition to readily volatile, also moderately and only slightly volatile components. The synthetic odorants embrace representatives from practically all classes of odorant substances. The following list comprises examples of known odorants which may be combined with the compounds of the invention:

natural products: tree moss absolute, basil oil, tropical fruit oils (such as bergamot oil, mandarin oil, etc.), mastix absolute, myrtle oil, palmarosa oil, patchouli oil, petitgrain oil, wormwood oil, lavender oil, rose oil, jasmine oil, ylang-ylang oil, etc.;

alcohols: farnesol, geraniol, linalool, nerol, phenylethyl alcohol, rhodinol, cinnamic alcohol, (Z)-hex-3-en-1-ol, menthol, a-terpineol, etc.;

aldehydes: citral, α-hexyl cinnamaldehyde, Lilial, methylionone, verbenone, nootkatone, geranylacetone, etc.;

esters: allyl phenoxyacetate, benzyl salicylate, cinnamyl propionate, citronellyl acetate, decyl acetate, dimethylbenzylcarbinyl acetate, dimethylbenzylcarbinyl butyrate, ethyl acetoacetate, cis-3-hexenyl isobutyrate, cis-3-hexenyl salicylate, linalyl acetate, methyl dihydrojasmonate, styralyl propionate, vetiveryl acetate, benzyl acetate, geranyl acetate, etc.;

lactones: γ-undecalactone, δ-decalactone, pentadecanolide, 12-oxahexadecanolide, etc.;

acetals: Viridine (phenylacetaldehyde dimethylacetal), etc.;

other components often used in perfumery: indole, p-mentha-8-thiol-3-one, methyleugenol, eugenol, anethol, etc.

The novel compounds of the invention harmonize particularly well with floral notes (lily of the valley, rose, iris, jasmine, ylang-ylang, narcissus notes, etc.) as well as with woody, chypre and animalic notes, tobacco like and patchouli compositions, etc.

The percentage in which the compounds of the invention are used in a composition may vary within wide limits ranging from a few parts per thousand in mass market products (e.g. cleaning compositions, deodorant, etc.) up to a few percents in alcoholic extracts for fine perfumery. In all cases, even in small amounts, the compounds of Formula I provide odorant compositions with green-galbanum and intense fresh green-fruity notes and a remarkable increase of the volume (strength, diffusivity) and of the duration (substantivity) of the odor.

In the present invention, there is no restriction regarding the type of formulations and the destination of the actual finished product. Thus, the compounds of the present invention may be combined with, for example, eau de cologne, toilet water, scented water, perfume, body care and cosmetic products such as cream, shampoo, soap, household products such as detergent, household cleaner, fabric softener, and the like.

The following examples are provided to further illustrate the process of the present invention. These examples are illustrative only and are not intended to limit the scope of the invention in any way.

In the following examples, all compounds were unambiguously identified by their $^1$H-NMR- (chemical shifts (δ) are given in ppm downfield from TMS; coupling constants J in Hz),IR- and MS-spectra. Examples 1–10 illustrate compounds of Formula I and R=A, and examples 11–15 illustrate compounds of Formula I and R=B.

EXAMPLES

Compounds of Formula I and R=A

Example 1

2-Cyclohexylhepta-1,6-dien-3-one a) 2-Cyclohexylprop-2-en-1-al

Successively, sulfuric acid 62% (79.4 g, 0.5 mol), aqueous formaldehyde 35% (82 g, 1.0 mol) and cyclohexyl acetaldehyde (100.8 g, 0.8 mol) were added slowly to diethylamine (73 g, 1.0 mol) at 0° C. After stirring at 80° C. overnight, the reaction mixture was extracted with MTBE. The combined organic phases were washed with $H_2O$ until neutral pH was achieved, dried ($MgSO_4$) and concentrated in vacuo. The crude product was distilled under reduced pressure using a Widmer column (10 Torr, 80° C.) yielding 89.5 g (81%) of pure product as colorless oil.

$^1$H-NMR (200 MHz, $CDCl_3$): 9.5 (s, 1H, —CHO), 6.22 (s, 1H, H—C(3)), 5.95 (s, 1H, H'—C(3)), 2.48 (m, 1H, —CH—), 1.9–1.6 (m, 5H, —$CH_2$—), 1.5–1.0 (m, 5H, —$CH_2$—). MS (EI): 138($M^+$,40), 123(22), 109(73), 95(90), 91(28), 79(61), 67(100), 55(39), 41(53). IR (neat): 2927vs, 2853 s, 1694vs, 1449m $cm^{-1}$.

b) 2-Cyclohexylhepta-1,6-dien-3-ol

2-Cyclohexylprop-2-en-1-al (69 g, 0.5 mol) in 100 ml of ether was slowly added to but-1-enylmagnesium bromide prepared by slow addition of 4-bromo-but-1-ene (81.0 g, 0.6 mol) in 100 ml of ether at 0° C. to magnesium turnings (13.2 g, 0.55 mol) in 300 ml of ether. After the addition was complete, the reaction mixture was allowed to warm to room temperature (RT) and was stirred for additional 3 hours. After quenching with 2N HCl, the organic phase was separated, washed with $H_2O$ until neutral pH was achieved, dried ($MgSO_4$), and the solvent was evaporated in vacuo. The crude product was distilled over a Vigreux column (0.15 Torr, 91° C.) yielding 85 g (88%) of pure product as colorless oil.

$^1$H-NMR (200 MHz, $CDCl_3$): 5.85 (ddt, J=17.2, 10.4, 6.6, 1H, H—C(6)), 5.05 (ddt, J=17.2, 2.0, 1.6, 1H, H—C(7)), 5.02 (dd, J=1.0, 1.0, 1H, H—C(1)), 4.98 (ddt, J=10.2, 2.1, 1.2, 1H, H'—C(7)), 4.88 (d, J=1.0, 1H, H'—C(1)), 4.09 (t, J=6.2, 1H, H—C(3)), 2.22–2.10 (m, 2H, H—C(5)), 1.89 (m, 1H, —CH—), 1.80–1.52 (m, 8H, —CH$_2$—, —OH), 1.38–1.24 (m, 5H, —CH$_2$—). MS (EI): 194(M$^+$,1), 176(4), 165(3), 151(9), 139(11), 122(11), 109(15), 95(37), 83(66), 79(43), 71(34), 67(50), 55(100), 41(50). IR (neat): 3361s, 2926vs, 2852s, 1641w, 1448m cm$^{-1}$.

c) 2-Cyclohexylhepta-1,6-dien-3-one

2-Cyclohexyl-hepta-1,6-dien-3-ol (85 g, 0.44 mol) were oxidized with MnO$_2$ (804 g, 9.2 mol) in 2 l of hexane at RT. After stirring for 96 hours, the reaction mixture was filtered over Celite and concentrated in vacuo yielding 71 g of a yellow oil. Distillation (0.04 Torr/70° C.) yielded 43.5 g (51%) of pure product.

Odor: green-galbanum, fruity-pineapple, metallic.

$^1$H-NMR (400 MHz, CDCl$_3$): 5.95 (s, 1H, H—C(1)), 5.85 (ddt, J=17.0, 10.2, 6.4, 1H, H—C(6)), 5.65 (d, J=1.2, 1H, H'—C(1)), 5.05 (ddt, J=17.1, 1.6, 1.6, 1H, H—C(7)), 4.96 (ddt, J=10.2, 1.6, 1.2, 1H, H'—C(7)), 2.78 (t, J=7.4, 2H, H—C(4)), 2.59 (m, 1H, —CH—), 2.35 (m, 2H, H—C(5)), 1.80–1.65 (m, 5H, —CH$_2$—), 1.41–1.28 (m, 4H, —CH$_2$—), 1.22–1.00 (m, 3H, —CH$_2$—).MS (EI): 192(M$^+$,11), 177(4), 163(50), 149(29), 137(78), 121(9), 109(65), 95(22), 81(34), 77(12), 67(100), 55(61), 41(29). IR (neat): 2926vs, 2852s, 1681vs, 1449m cm$^{-1}$.

Examples 2–8 were prepared according to the general procedure described for Example 1. Only the spectroscopic data and olfactory properties are given below.

Example 2

2-Cyclopentylhepta-1,6dien-3-one

Odor: green-galbanum, anisic, metallic $^1$H-NMR (400 MHz, CDCl$_3$): 5.95 (s, 1H, H—C(1)), 5.85 (ddt, J=17.2, 10.4, 6.6, 1H, H—C(6)), 5.70 (d, J=1.2, 1H, H'—C(1)), 5.04 (ddt, J=17.1, 1.8, 1.6, 1H, H—C(7)), 4.98 (ddt, J=10.2, 1.6, 1.2, 1H, H'—C(7)), 2.95 (m, 1H, —CH—), 2.80 (t, J=7.5, 2H, H—C(4)), 2.40 (m, 2, H—C(5)), 1.94–1.81 (m, 2H, —CH$_2$—), 1.75–1.55 (m, 4H, —CH$_2$—), 1.35–1.12 (m, 2H, —CH$_2$—). MS (EI): 178(M$^+$,1), 163(2), 149(18), 137(5), 123(43), 110(8), 95(100), 83(9), 79(15), 67(73), 55(61), 41(23). IR (neat): 2953vs, 2869s, 1681vs, 1641m cm$^{-1}$.

Example 3

2-(4-Methylcyclohexyl)hepta-1,6-dien-3-one (cis/trans isomers ~1:1)

Odor: green-galbanum, fruity-pineapple $^1$H-NMR (400 MHz, CDCl$_3$): 5.96+5.95 (2s, 1H, H—C(1)), 5.83 (ddt, J=17.2, 10.4, 6.6, 1H, H—C(6)), 5.69+5.65 (2d, J=1.4, 1H, H'—C(1)), 5.00 (m, 2H, H—C(7)), 2.77 (t, J=7.6, 2H, H—C(4)), 2.55 (m, 1H, —CH—), 2.35 (m, 2H, H—C(5)), 1.94–1.22 (m, 7H,—CH—, —CH$_2$—), 1.19–1.00 (m, 2H, —CH$_2$—), 1.00+0.89 (2d, J=7.2, 6.4, 3H, —CH$_3$). MS (EI): 206 (M$^+$,4), 191(6), 177(44), 163(7), 151(44), 149(33), 123(22), 110(17), 109(17), 107(14), 105(10), 95(34), 81(100), 79(24), 67(42), 55(65), 41(28). IR (neat): 2922vs, 2850s, 168vs, 1641m cm$^{-1}$.

Example 4

2-(3-Methylcyclohexyl)hepta-1,6-dien-3-one (cis/trans isomers ~1:1)

Odor: green-fruity, pineapple with galbanum-aspects $^1$H-NMR (400 MHz, CDCl$_3$): 5.96+5.95 (2s, 1H, H—C(1)), 5.83 (ddt, J=16.8, 10.4, 6.6, 1H, H—C(6)), 5.70 (2d, J=1.2, 1H, H'—C(1)), 5.00 (m, 2H, H—C(7)), 2.9 (m, 0.5H, —CH—), 2.77 (m, 2H, H—C(4)), 2.61 (m, 0.5H, —CH—), 2.46 (m, 2H, H—C(5)), 2.01–1.09 (m, 9H, —CH—, —CH$_2$—), 1.03+0.88 (2d, J=7.2, 6.8, 3H, —CH$_3$). MS (EI): 206(M$^+$,4), 191(6), 177(30), 163(18) 151(49), 149(11), 123 (20), 110(22), 109(15), 107(13), 105(8), 95(33), 81(100), 79(22), 67(42), 55(60), 41(28). IR (neat): 2923vs, 2850s, 1681vs,1641m cm$^{-1}$.

Example 5

2-(2-Methylcyclohexyl)hepta-1,6-dien-3-one (cis/trans isomers ~1:1)

Odor: green-galbanum, mushroom, fruity-pineapple with jasmine aspects $^1$H-NMR (400 MHz, CDCl$_3$): 6.06+6.02 (2s, 1H, H—C(1)), 5.82 (m, 1H, H—C(6)), 5.70+5.52 (2d, J=1.2, 1H, H'—C(1)), 5.00 (m, 2H, H—C(7)), 2.80 (m, 2.5H, H—C(4), —CH—), 2.38 (m, 2H, H—C(5)), 1.95 (m, 0.5H, —CH—), 1.82–1.00 (m, 9H,—CH—, —CH$_2$—), 0.71+0.69 (2d, J=6.4, 7.2, 3H, —CH$_3$). MS (EI): 206(M$^+$,15), 191(10), 177(33), 164(23) 151(50), 149(32), 133(124), 123(27), 109 (28), 107(22), 105(22), 95(49), 81(89), 79(35), 67(51), 55(100), 41(44). IR (neat): 2925vs, 2853s, 1681vs, 1641m cm$^{-1}$.

Example 6

2-(2-Methylcyclopentyl)hepta-1,6-dien-3-one (cis/trans isomers)

Odor: green-galbanum, pineapple, grapefruit with anisic aspects $^1$H-NMR (400 MHz, CDCl$_3$): 6.08+6.01 (2s, 1H, H—C(1)), 5.82 (m, 1H, H—C(6)), 5.70+5.66 (2d, J=1.2, 1H, H'—C(1)), 5.02 (m, 2H, H—C(7)), 3.10–1.20 (5m, 12), 0.90+0.54 (2d, J=6.4, 6.8, 3H, —CH$_3$). MS (EI): 192(M$^+$,4), 177(14), 163(68), 150(23), 137(63), 133(124), 123(11), 119 (25), 109(63), 107(23), 105(9), 95(37), 81(56), 79(33), 67(95), 55(100), 41(47). IR (neat): 2954vs, 2869s, 1681vs, 1641m cm$^{-1}$.

Example 7

2-Cycloheptylhepta-1,6-dien-3-one

Odor: green-galbanum, fruity, floral (lindenblossom)

$^1$H-NMR (400 MHz, CDCl$_3$): 5.95 (s, 1H, H—C(1)), 5.85 (ddt, J=17.2, 10.4, 6.4, 1H, H—C(6)), 5.68 (d, J=1.2, 1H, H'—C(1)), 5.05 (ddt, J=17.2, 1.6, 1.6, 1H, H—C(7)), 4.96 (ddt, J=10.4, 1.6, 1.2, 1H, H'—C(7)), 2.77 (t, J=7.2, 2H, H—C(4)), 2.72 (m, 1H, —CH—), 2.37 (m, 2H, H—C(5)), 1.74–1.29 (m, 12H, —CH$_2$—). MS(EI): 206(M$^+$,3), 191(2), 177(27), 165(9), 151(38), 149(22), 135(6), 123(11), 121 (13), 109(22), 95(30), 81(100), 67(96), 55(100), 41(51). IR (neat): 2924vs, 2855s, 1680vs, 1641m cm$^{-1}$.

Example 8

2-Cyclooctylhepta-1,6-dien-3-one

Odor: green-galbanum, woody, fatty with marine aspects $^1$H-NMR (400 MHz, CDCl$_3$): 5.95 (s, 1H, H—C(1)), 5.85 (ddt, J=17.1, 10.1, 6.6, 1H, H—C(6)), 5.69 (d, J=1.1, 1H, H'—C(1)), 5.05 (ddt, J=17.1, 1.7, 1.7, 1H, H—C(7)), 4.96 (ddt, J=10.2, 1.6, 1.2, 1H, H'—C(7)), 2.96 (m, 1H, —CH—), 2.75 (t, J=7.4, 2H, H—C(4)), 2.35 (m, 2H, H—C(5)), 1.80–1.45 (m, 14H, —CH$_2$—). MS(EI): 220(M$^+$,4), 205(2), 191(30), 179(19), 177(14), 149(28), 137(15), 135(17), 123 (21), 121(24), 109(32), 110(22), 95(94), 81(79), 67(54), 55(100), 41(47). IR (neat): 2920vs, 2851s, 1680vs, 1641m cm$^{-1}$.

Example 9

3-Cyclohexylocta-2,7-dien-4-one a) 3-Cyclohexylbut-2-enal

A mixture of [(2-cyclohexylethenyl)oxy)]trimethylsilane (19.8 g, 0.1 mol) and acetaldehyde (4.4 g, 0.1 mol) was added slowly at −70° C. to a mixture of titantetrachloride (11 ml, 0.1 mol) and titanium(IV) isopropoxide (0.59 ml, 0.02 mol) in $CH_2Cl_2$ (50 ml). After stirring for 1 hour, the reaction was quenched with saturated $NH_4Cl$ -solution and extracted twice with ether (2×100 ml). The combined organic phases were washed to neutral pH, dried ($MgSO_4$) and concentrated in vacuo. The crude product was dehydrated by distillation with $I_2$ (200 mg) over a 5 cm Widmer column (0.1 Torr, 120° C.) yielding 7.7 g (50%) of 3-cyclohexylbut-2-enal as E/Z-mixture of ~7:1.

$^1$H-NMR ((E)-isomer, 200 MHz, $CDCl_3$): 9.31 (d, J=1.0, 1H, —CHO), 6.48 (q, J=7.5, 1H, H—C(3)), 2.55 (m, 1H, —CH—), 2.05 (d, J=7.5, 3H, $CH_2$), 2.00–1.05 (m, 10H, —$CH_2$—). MS (EI): 152($M^+$,72), 137(29), 134 (14), 123 (100), 119(24), 109(43), 105(25), 95(57), 91(37), 84(21), 81(68), 79(45), 77(24), 69(31), 67(72), 55(48), 41(50). IR (neat): 2927vs, 2853s, 2704w, 1689s, 1634m, 1449m $cm^{-1}$.

b) 3-Cyclohexylocta-2,7-dien-4-one (E/Z mixture of 10:1)

3-Cyclohexylocta-2,7-dien-4-one was prepared following the experimental procedure described in Examples 1a and 1c.

Odor: green-galbanum, pineapple, cassis $^1$H-NMR ((E)-isomer, 400 MHz, $CDCl_3$): 6.50 (q, J=7.0, 1H, H—C(2)), 5.80 (ddt, J=16.8, 10.4, 6.4, 1H, H—C(7)), 5.01 (ddt, J=17.1, 1.6, 1.6, 1H, H—C(8)), 4.96 (ddt, J=10.2, 1.8, 1.2, 1H, H'—C(8)), 2.68 (t, J=7.6, 2H, H—C(5)), 2.55 (tt, J=12.2, 3.4, 1H, —CH—), 2.35 (m, 2H, H—C(6)), 1.88 (d, J=6.8, —$CH_3$), 1.85–1.60 (m, 5H, —$CH_2$—), 1.50–1.10 (m, 5H, —$CH_2$—). MS (EI): 206($M^+$,10), 191(15), 177(16), 164 (9), 151 (100), 123(19), 109(8), 95(12), 81(80), 79(18), 67(43), 55(49), 41(20). IR (neat): 2926vs, 2852s, 1672s, 1641m, 145m $cm^{-1}$.

Example 10

4-Cyclohexylnona-3,8-dien-5-one (20:1 E/Z mixture)

4-Cyclohexylnona-3,8-dien-5-one was prepared according to the general procedure described for 3-cyclohexylocta-2,7-dien-4-one (Example 9).

Odor: green-fruity, apple, pineapple, galbanum, anisic $^1$H-NMR ((E)-isomer, 400 MHz, $CDCl_3$): 6.35 (t, J=7.4, 1H, H—C(3)), 5.82 (ddt, J=17.0, 10.4, 6.4, 1H, H—C(8)), 5.01 (ddt, J=17.1, 1.8, 1.7, 1H, H—C(9)), 4.96 (ddt, J=10.2, 1.8, 1.2, 1H, H'—C(9)), 2.70 (t, J=7.6, 2H, H—C(6)), 2.51 (tt, J=12.0, 3.6, 1H, —CH—), 2.39–2.30 (m, 2H, H—C(7)), 2.29 (q, J=7.6, H—C(2)), 1.82–1.60 (m, 5H, 13 $CH_2$—), 1.45 (m, 2H, —$CH_2$—), 1.32–1.18 (m, 3H, —$CH_2$—), 1.08 (t, J=7.6, —$CH_3$). MS (EI, (E)-isomer): 220($M^+$,10), 191 (43), 177(9), 165 (100), 149 (5), 137(11), 123(7), 109(12), 95(86), 81(72), 79(23), 67(34), 55(63), 41(26). IR (neat): 2927vs, 2852s, 1672s, 1641m, 1450m $cm^{-1}$.

Example 11

1-(1,4,4a,5,6,7,8,8a-Octahydronaphth-2-yl)pent-4-ene-1-one 1-(3,4,4a,5,6,7,8,8a-Octahydronaphth-2-yl)pent-4-ene-1-one 1-(1,2,3,4,5,6,7,8-Octahydronaphth-2-yl)pent-4-ene-1-one a) 2-Ethynyldecahydronaphthalen-2-ol Acetylene was bubbled for 4 hours through a mixture of tBuOK (95.8 g, 0.85 mol) in THF (11) at 0° C. 2-Decalone (100 g, 0,66 mol) was added slowly at RT to the slightly yellow suspension and the resulting mixture was stirred for additional 3.5 hours, quenched with saturated $NH_4Cl$ (500 ml) solution, and extracted with MTBE (2×700 ml). The combined organic phases were washed with $NH_4Cl$ (500 ml), $H_2O$ (2×500 ml), saturated NaCl (500 ml) solution until neutral pH was achieved, dried ($MgSO_4$), and concentrated in vacuo. The crude orange oil was flash distilled (0.01 Torr, 88–90° C.) yielding 100.6 g (86%) of 2-ethynyldecahydronaphthalen-2-ol.

b) 2-(Pent-4-en-1-ynyl)decahydronaphth-2-ol

A solution of 2-ethynyldecahydronaphthalen-2-ol (100.6 g, 0.56 mol) in iPrOH (300 ml) was added slowly at 0° C. under a nitrogen atmosphere to a mixture of KOH (47.5 g), $K_2CO_3$ (6.5 g), and CuCl (4.4 g) in MeOH (300 ml). After stirring for additional 30 minutes at 0° C., allylbromide (102 g, 0.85 mol) was added slowly over a period of 25 minutes. The reaction mixture was stirred overnight at RT, quenched with $NH_4Cl$ and concentrated in vacuo. The residue was taken up in saturated $NH_4Cl$ (500 ml) solution, extracted with MTBE (2×400 ml). The combined organic phases were washed with saturated $NH_4Cl$ solution (500 ml), $H_2O$ (2×500 ml), saturated NaCl solution (500 ml) until neutral pH was achieved, dried ($MgSO_4$), and evaporated in vacuo to yield quantitatively 120 g of crude product which was used without further purification in the next step.

c) 1-(1,4,4a,5,6,7,8,8a-Octahydronaphth-2-yl)pent-4-ene-1-one 1-(3,4,4a,5,6,7,8,8a-Octahydronaphth-2-yl)pent-4-ene-1-one 1-(1,2,3,4,5,6,7,8-Octahydronaphth-2-yl)pent-4-ene-1-one A solution of 2-(pent-4-en-1-ynyl)decahydronaphalen-2-ol (120 g, 0.55 mol) in HCOOH 80% (200 ml) was heated at 90° C. for 16 h. After cooling to RT, the resulting brown mixture was neutralized with saturated $Na_2CO_3$ and extracted with MTBE (2×400 ml). The combined organic phases are washed with $NaHCO_3$ (2×400 ml), $H_2O$ (2×400 ml) and dried over $MgSO_4$. After distillation with a Vigreux column, 54.2 g (45%) of the olfactorily pure product was obtained as a mixture of 5 isomers.

Odor (mixture of 5 isomers): green-galbanum, fruity $^1$H-NMR (200 MHz, $CDCl_3$): 6.90 (m, ~0.9H), 6.85 (m, 1H), 5.00 (m, 2H), 2.82–1.20 (m, 18H). MS (EI): Peak 1 (22%): 218($M^+$,18), 176(6), 163(30), 135(100), 119(7), 107 (9), 105(8), 93(23), 91(38), 79(22), 67(24), 55(33), 41(12); Peak 2 (8%): 218($M^+$,55), 177(54), 163(100), 145(19), 135(92), 119(13), 107(24), 105(18), 93(47), 91(57), 79(49), 67(68), 55(54), 41(25); Peak 3 (15%): 218($M^+$,46), 177(50), 163(87), 145(19), 135(100), 119(12), 107(24), 105(16), 93(47), 91(50), 79(47), 67(67), 55(47), 41(27); Peak 4 (13%): 218($M^+$,11), 177(1), 163(100), 145(2), 135(11), 107 (7), 93(25), 91(15), 79(20), 67(20), 55(18), 41(11); Peak 5 (42%): 218($M^+$,8), 177(2), 163(100), 145(4), 135(11), 107 (12), 93(24), 91(16), 79(21), 67(21), 55(20), 41(11). IR (mixture of 5 isomers, neat): 2923s, 2853m, 1669vs, 1640m $cm^{-1}$.

The main and most powerful isomer, cis-1-(1,4,4a,5,6,7,8,8a-octahydronaphth-2-yl)pent-4-ene-1-one, with a GC-odor threshold of 10 pg was isolated by preparative GLC for $^1$H-NMR analysis. $^1$H-NMR (400 MHz, $CDCl_3$): 6.85 (m, 1H, CH=C), 5.85 (ddt, 1H, J=17.0, 10.2, 6.6, H—C(4)), 5.05 (ddt, J=17.1, 1.6, 1.6, 1H, H—C(5)), 4.98 (ddt, J=10.1, 1.8, 1.2, H'—C(5)), 2.74 (t, J=7.6, H—C(2)), 2.35 (m, 2H, —$CH_2$—), 2.30–2.13 (m, 4H, —$CH_2$—), 1.85 (m, 2H,—CH—), 1.57 (m, 2H, —$CH_2$—), 1.47–1.32 (m, 6H, —$CH_2$—).

The compounds of Examples 12–15 were prepared according to the general procedure described in Example 11.

Only the spectroscopic data and olfactory properties for each example are given below.

Example 12

1-(2,3,3a,4,7,7a-hexahydro-1H-indene-5-yl)pent-4-ene-1-one 1-(2,3,3a,6,7,7a-hexahydro-1H-indene-5-yl)pent4-ene-1-one 1-(2,3,4,5,6,7-hexahydro-1H-indene-5-yl)pent-4-ene-1-one Odor (mixture of 3 isomers): green-galbanum, cassis, boysenberry, metallic $^1$H-NMR (200 MHz, CDCl$_3$): 6.90 (m, ~0.8H), 6.85 (m,1H), 5.00 (m, 2H), 2.82–1.20 (m, 16H). MS (EI): Peak 1 (16%): 204(M$^+$,18), 162(7), 149(34), 121(100), 107(5), 105(7), 93(25), 91(37), 79(39), 67(14), 55(35), 41(11); Peak 2 (61%): 204(M$^+$,14), 163(16), 149(100), 131(17), 121(22), 107(13), 105(11), 93(25), 91(23), 79(34), 67(12), 55(18), 41(10); Peak 3 (23%): 204(M$^+$,7), 163(2), 149(100), 131(6), 121(7), 107(5), 107(7), 93(26), 91(16), 79(32), 67(13), 55(19), 41(9). IR (mixture of 3 isomers, neat): 2943s, 2867m, 1710w, 1668vs, 1639m cm$^-$.

Example 13

1-(4a-Methyl-3,4,4a,5,6,7,8,8a-octahydronaphth-2-yl)pent4-ene-1-one 1-(4a-Methyl-1,4,4a,5,6,7,8,8a-octahydronaphth-2-yl)pent4-ene-1-one Odor (mixture of 4 isomers): violet, woody, green-galbanum, pineapple $^1$H-NMR (200 MHz, CDCl$_3$): 6.85+6.75 (2m, 1H, CH=C), 5.85 (m, 1H, CH=CH$_2$), 5.00 (m, 2H, CH=CH$_2$), 2.75 (m, 2H), 2.60–1.00(m, 15H), 0.95+0.89+0.78 (3s, 3H). MS (EI): Peak 1 (32%): 232(M$^+$,56), 217(32), 204(3), 191(44), 177(100), 159(20), 149(26), 135(18), 121(16), 109 (84), 96(23), 93(24), 91(55), 81(52), 79(39), 67(65), 55(68), 41(30); Peak 2 (52%): 232(M$^+$,15), 217(5), 204(3), 191(2), 177(100), 159(3), 149(16), 137(7), 121(3), 109(9), 107(9), 96(10), 93(13), 91(16), 81(73), 67(14), 55(23), 41(10); Peak 3 (2%): 232(M$^+$,46), 217(25), 191(35), 177(43), 161(12), 159(11), 149(100), 135(13), 121(12), 109(70), 107(27), 93(42), 91(48), 81(52), 67(55), 55(67), 41(30); Peak 4 (14%): 232(M$^+$,8), 217(3), 204(2), 191(2), 177(100), 159 (3), 149(8), 121(5), 109(7), 107(16), 93(16), 91(12), 81(34), 67(14), 55(20), 41(10); IR (mixture of 4 isomers, neat): 2925vs, 2860s, 1668vs, 1640m cm$^1$.

Example 14

1-(4-Methyl-1,4,4a,5,6,7,8,8a-octahydronaphth-2-yl)pent-4-ene-1-one 1-(4-Methyl-3,4,4a,5,6,7,8,8a-octahydronaphth-2-yl)pent-4-ene-1-one 1-(4-Methyl-1,2,3,4,5,6,7,8-octahydronaphth-2-yl)pent4-ene-1-one Odor (mixture of 3 isomers): woody, green-galbanum, fruity, fatty $^1$H-NMR (200 MHz, CDCl$_3$): 6.62+6.59 (2m, ~0.8H, CH=C), 5.82 (m, 1H, CH=CH$_2$), 5.00 (m, 2H, CH=CH$_2$), 2.75 (m, 2H), 2.68–0.70(m, 18H). MS (EI): Peak 1 (11%): 232(M$^+$,4), 217(1), 203(3), 190(8), 177(22), 159(3), 149 (100), 133(14), 121(16), 119(8), 105(37), 91(39), 81(24), 79(22), 67(15), 55(53), 41(20); Peak 2 (56%): 232(M$^+$,42), 217(5), 203(3), 191(33), 177(100), 159(11), 149(75), 135 (9), 133(14), 121(16), 109(31), 107(26), 93(40), 91(44), 81(48), 67(57), 55(74), 41(44); Peak 3 (33%): 232(M$^+$,78), 217(7), 203(3), 191(73), 177(100), 159(15), 149(32), 135 (13), 121(21), 109(57), 107(35), 93(47), 91(43), 81(56), 67(68), 55(80), 41(50). IR (mixture of 3 isomers, neat): 2922vs, 2852s, 1711m, 169vs, 1640m cm$^1$.

Example 15

1-(3a,4,5,6,7,7a-hexahydro-1H-indene-2-yl)pent-4-ene-1-one 1-(2,3,4,5,6,7-hexahydro-1H-indene-2-yl)pent-4-ene-1-one Odor (mixture of 3 isomers): fruity, pineapple, green-galbanum $^1$H-NMR (400 MHz, CDCl$_3$): 6.69 (m, 0.8H, CH=C), 5.83 (m, 1H, CH=CH$_2$), 5.05 (m, 1H, CH=CH$_2$), 4.98 (m, 1H, CH=CH$_2$), 2.75 (m, 2H), 2.60–2.20 (m, 5H), 1.90 (m, 1H), 1.78–0.25 (m, 8H). MS (EI): Peak 1 (3%): 204(M$^+$,5), 149(3), 121(100), 105(3), 93(20), 91(13), 79(30), 77(12), 67(12), 55(13), 41(6); Peak 2 (16%): 204(M$^+$,16), 189(9), 162(4), 149(34), 131(2), 121(100), 107(9), 105(5), 93(18), 91(28), 79(27), 77(14), 67(11), 55(20), 41(9); Peak 3 (79%): 204(M$^+$,12), 189(1), 163(14), 149(100), 131(11), 121(47), 107(7), 105(8), 93(29), 91(21), 79(37), 77(17), 67(14), 55(18), 41(9); IR (mixture of 3 isomers, neat): 2925vs, 2851s, 1667vs, 1641m cm$^-$.

Example 16

Feminine Composition for Toiletries

|  | parts per weight |
| --- | --- |
| Adoxal (10% DPG) | 10 |
| Ambrofix | 3 |
| Beta-ionone | 10 |
| Bergamote oil abergapt | 50 |
| Calone 1951 (10% DPG) | 10 |
| Cepionate | 200 |
| Citronellol | 30 |
| Dasmascenone (10% DPG) | 10 |
| Dihydromyrcenol | 30 |
| Ethyllinalool | 40 |
| Florhydral | 5 |
| Galaxolide 50% PHT | 200 |
| α-Hexyl cinnamic aldehyde | 80 |
| Phenylethyl alcohol | 50 |
| Indol (10% DPG) | 5 |
| Iso E super | 40 |
| Isoraldeine 95 | 50 |
| Jasmone cis (10% DPG) | 10 |
| Lilial | 50 |
| Melonal (10% DPG) | 5 |
| Methyl anthranilate (10% DPG) | 10 |
| Methyl pamplemousse (1,1-dimethoxy-2,2,5-trimethyl-4-hexene) | 20 |
| Nectaryl | 2 |
| Radjanol | 20 |
| Tropional | 15 |
| Tricyclal (10% DPG) | 10 |
| Vanilline (10% DPG) | 5 |
| Viridine (10% DPG) | 10 |
| Ylang Ylang oil. | 10 |
| 2-Cyclohexyl-hepta-1,6-dien-3-one (10% DPG) | 10 |
|  | 1000 |

In this feminine accord, 2-cyclohexyl-hepta-1,6-dien-3-one enhances the fruity hesperidic part giving a vibrant character to the fragrance. Its long-lasting effect is very useful to keep the fragrance fresh over time.

Example 17

Green-marine Composition for Toiletries

| | parts per weight |
|---|---|
| Acetal CD (phenylacetaldehyde glycerylacetal) | 40 |
| Acetal R (acetaldehyde phenylethyl propyl acetal) | 2 |
| Adoxal 10% DPG (2,6,10-trimethyl-9-undecenal) | 1.5 |
| Phenoxyethyl alcohol | 70 |
| Linalyl benzoate | 100 |
| Bigarade oil | 10 |
| Clonal (10% DPG) | 5 |
| Beta-damascone | 5 |
| Dimetol (2,6-dimethyl-2-heptanol) | 25 |
| Disopropylene glycol | 375 |
| Florhydral | 20 |
| Glycolierral | 60 |
| (Z)-Hex-3-en-1-ol | 5 |
| (Z)-Hex-3-en-1-yl acetate | 2.5 |
| (Z)-Hex-3-en-1-yl formiate | 5 |
| (Z)-Hex-3-en-1-yl salycilate | 5 |
| Hexyl propionate | 10 |
| Beta-ionone | 10 |
| Linalool | 100 |
| Linalool oxyde (1% DPG) | 2.5 |
| Melonal (10% DPG) | 2.5 |
| Menthe Crepue Ess USA (10% DPG) | 10 |
| Nerol | 80 |
| Nerolidol | 40 |
| Radjanol | 5 |
| Viridine (10% PE) | 5 |
| 2-Cyclohexylhepta-1,6-dien-3-one | 4 |
| | 1000 |

The new compound, namely 2-cyclohexylhepta-1,6-dien-3-one, brings a fresh, natural galbanum note to the perfumed composition, enhancing its diffusion and adding a fresh pineapple top note.

Example 18

Floral Composition for Fabric Softener

| | parts per weight |
|---|---|
| Acetate PA (2-propenyl phenoxyacetate) | 15 |
| Allyl amyl glycolate | 15 |
| Ambrofix | 1 |
| Benzyl acetate | 60 |
| Citronellol extra | 50 |
| Citronellyl acetate | 30 |
| Cyclal C | 10 |
| Dihydromyrcenol | 50 |
| Ebanol | 10 |
| Freskomenthe | 5 |
| Galaxolide 50% PHT | 60 |
| Geranitrile | 12 |
| Givescone | 7 |
| α-Hexylcinnamic aldehyde | 200 |
| Iso E Super | 30 |
| Linalool | 60 |
| Lilial | 60 |
| Nectaryl | 5 |
| Neroline crist. | 5 |
| Rosacetol | 20 |
| Roseoxyde | 8 |
| Terpineol | 60 |
| 10-Undecenal | 2 |

-continued

| | parts per weight |
|---|---|
| Verdyl acetate | 200 |
| Ylang Oil | 15 |
| 2-Cyclohexylhepa-1,6-dien-3-one (10% DPG) | 10 |
| | 1000 |

In this floral accord, 2-cyclohexylhepta-1,6-dien-3-one with its green-galbanum note gives a fresh and clean effect to the fragrance, both on wet and on dry laundry.

Example 19

Fresh Floral Composition for Softeners

| | parts per weight |
|---|---|
| Adoxal (10% DPG) | 1 |
| Agrumex | 40 |
| Amberketal (10% IPM) | 15 |
| Ambretone | 10 |
| Bigarade oil | 20 |
| Citronellol | 35 |
| Beta-Damascone | 2.5 |
| Dimethylbenzylcarbinyl acetate | 75 |
| Ebanol | 20 |
| Fixambrene | 10 |
| Florhydral | 10 |
| Gardenol | 7.5 |
| α-Hexylcinnamic aldehyde | 70 |
| Hexyl salicylate | 100 |
| Beta-ionone | 40 |
| Isoraldeine | 30 |
| Jasmine reconst. | 15 |
| Jasmonyl | 25 |
| Lilial | 70 |
| 2-Methylundecanal | 5 |
| Oranger crystals | 4 |
| Phenylethylalcohol | 85 |
| Rosacetol | 30 |
| Tetrahydrolinalool | 100 |
| Thibetolide | 20 |
| Undecavertol | 25 |
| 9-Undecenal | 5 |
| Verdylpropionate | 55 |
| Vertofix coeur | 55 |
| 1-(1,4,4a,5,6,7,8,8a-Octahydronaphth-2-yl)pent-4-ene-1-one | 20 |
| 1-(3,4,4a,5,6,7,8,8a-Octahydronaphth-2-yl)pent-4-ene-1-one | |
| | 1000 |

The novel compound adds a fresh, fruity galbanum note to the perfumed composition, enhancing its volume, diffusion, and long-lastingness.

For the exact definition of the compound/composition names mentioned above, see Flavor and Fragrance materials 1998, Allured Publishing Corporation, Carol Stream, Ill., U.S.A. or Arctander, Perfume and Flavor Chemicals (1969), published by the author, Montclair, N.J., U.S.A.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound of formula I

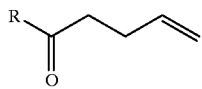
(I)

wherein R is a residue A

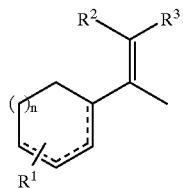
(A)

or a residue B

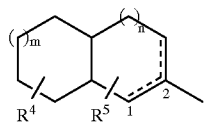
(B)

and $R^1$, $R^2$, $R^3$, $R^4$, and $R^5$ are independently hydrogen, methyl or ethyl, and further wherein $R^1$, $R^4$, and $R^5$ are located at any position of the ring structure, n and m are independently 0, 1, 2, or 3 and the dotted lines represent in formula A an optional double bond and in formula B a double bond either in position 1 or 2.

2. A compound according to claim 1 of formula Ia

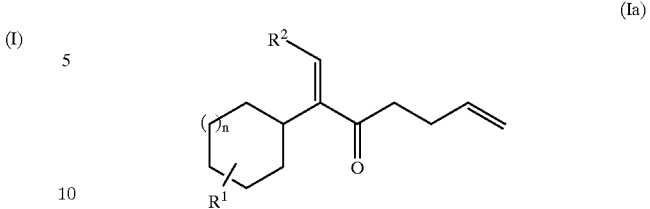
(Ia)

wherein $R^1$ and $R^2$ are independently hydrogen or methyl and n is for 0 or 1.

3. A compound according to claim 1 wherein the compound is 2-Cyclohexylhepta-1,6-dien-3-one according to claim 1.

4. A compound according to claim 1 wherein the compound is (E)- and/or (Z)-3-Cyclohexylocta-2,7-dien-4-one.

5. A compound according to claim 1 wherein the compound is 2-Cyclopentylhepta-1,6-dien-3-one.

6. A compound according to claim 1 wherein the compound is 1-(3,4,4a,5,6,7,8,8a-Octahydronaphth-2-yl)pent-4-ene-1-one.

7. A compound according to claim 1 wherein the compound is 1-(1,4,4a,5,6,7,8,8a-Octahydronaphth-2-yl)pent-4-ene-1-one.

8. A composition comprising at least 1 compound according to claim 1.

9. A composition according to claim 8 comprising 1-(3,4,4a,5,6,7,8,8a-Octahydronaphth-2-yl)pent-4-ene-1-one and 1-(1,4,4a,5,6,7,8,8a-Octahydronaphth-2-yl)pent-4-ene-1-one.

10. A composition according to claim 8 wherein the composition exhibits a green-galbanum fresh (metallic type) and fruity-pineapple and/or fruity-cassis odor.

* * * * *

UNITED STATES PATENT AND TRADEMARK OFFICE
CERTIFICATE OF CORRECTION

PATENT NO. : 6,184,419 B1
DATED : February 6, 2001
INVENTOR(S) : Katja Berg-Schultz et al.

It is certified that error appears in the above-identified patent and that said Letters Patent is hereby corrected as shown below:

<u>Title page,</u>
Item [73] Assignee, delete "Givaudan Roure (International) SA", and insert
-- Givaudan SA --.

Signed and Sealed this

Twenty-eighth Day of August, 2001

Attest:

*Attesting Officer*

NICHOLAS P. GODICI
*Acting Director of the United States Patent and Trademark Office*